United States Patent [19]
Nelson et al.

[11] Patent Number: 4,883,831
[45] Date of Patent: Nov. 28, 1989

[54] MELAMINE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 284,574

[22] Filed: Dec. 15, 1988

[51] Int. Cl.$^4$ .............................................. C08K 5/34
[52] U.S. Cl. ..................... 524/100; 524/98; 544/198
[58] Field of Search ................. 524/98, 100; 544/198

[56] References Cited
U.S. PATENT DOCUMENTS

| | | | |
|---|---|---|---|
| 3,488,290 | 1/1970 | Gerhardt et al. | 524/39 |
| 3,496,134 | 2/1970 | DiGiaimo | 524/100 |
| 3,684,765 | 8/1972 | Matsui et al. | 524/99 |
| 4,348,493 | 9/1982 | Loffelman | 524/100 |
| 4,670,488 | 6/1987 | Maegawa et al. | 524/99 |

Primary Examiner—John Kight
Assistant Examiner—Kriellion S. Morgan
Attorney, Agent, or Firm—William E. Dickheiser

[57] ABSTRACT

Melamine-based compounds having a multiplicity of 2,2,6,6-tetraalkyl piperidine moieties are light stabilizers for organic polymers.

8 Claims, No Drawings

MELAMINE-BASED LIGHT STABILIZERS FOR PLASTICS

The invention is directed to polymeric compositions which are resistant to degradation and discoloration when exposed to actinic radiation. In particular, it is directed to resins such as polypropylene, polyethylene, etc., which are stabilized with an effective amount of melamine derivatives which contains the 2,2,6,6-tetraalkylpiperidine moiety. The invention is further directed to a novel group of compounds which are useful as additives for synthetic polymers which act to retard photodegradation.

Many synthetic organic polymers deteriorate rapidly when exposed to sunlight. To circumvent this rapid degradation many additives have been developed to stabilize these resins against the harmful radiation. Among these additives are the UV absorbers such as the hydroxybenzophenones and the hydroxyphenylbenzotriazoles, the organonickel complexes which serve to quench excited states, and most recently the hindered amine light stabilizers (HALS). The HALS possess the 2,2,6,6-tetraalkylpiperidine group that is most common substituted in the 4-position and act as radical scavengers, thus inhibiting the degradation process.

Among the requirements for a compound to be an effective light stabilizer are the need for it to be compatible with the resin in which it is to be incorporated, sufficiently nonvolatile so as to remain in the resin during and after processing at elevated temperatures and be resistant to extraction by water. Of the piperidine compounds disclosed to date, those that are connected to a triazine ring are in many cases preferred because they more fully meet the criteria mentioned above.

Although the compounds of the prior art are, in general, effective light stabilizers for synthetic organic polymers, none of them completely satisfy the stabilization requirements of polymers in their wide variety of forms and application. This is paricularly true for those polymeric materials that are used in thin articles, such as fibers and films. Because of these deficiencies, there remains a need for new substances which meet the requirements more fully.

The present invention discloses the stabilization of synthetic polymers by the incorporation of effective amounts of novel melamine compounds which possess the polyalkylpiperidine moiety. The melaminebased HALS may be one selected from those described by formula (I):

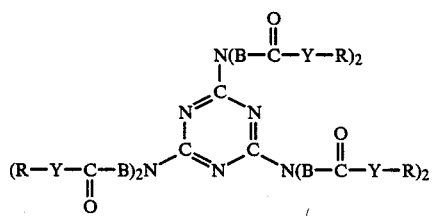

wherein R is the group

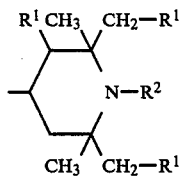

$R^1$ is selected from hydrogen and an alkyl group of 1–5 carbon atoms such as methyl, ethyl, n-propyl, etc., and is preferably hydrogen and methyl and most preferably hydrogen;

$R^2$ is independently selected from hydrogen, oxyl, hydroxyl, a straight or branched chain methylene-linked alkyl group of 1–18 carbon atoms such as methyl, ethyl, octyl, octadecyl, or 2-ethylhexyl, an alkanoyl group having 2–18 carbon atoms such as acetyl, propanoyl, butanoyl, isopentanoyl, or stearoyl, an alkenyl group of 3–4 carbon atoms, an alkenoyl group of 3–6 carbon atoms such as acryloyl, methacryloyl, crotonyl, an alkynyl group of 3–6 carbon atoms such as propargyl or 2-butynyl, a cyanomethyl group, a 2,3-epoxypropyl group, benzyl, alkylbenzyl group of 7–15 carbon atoms, or a 3,5-di-tert-butyl-4-hydroxybenzyl, 3-tert-butyl-4-hydroxybenzyl or 3-tert-butyl-4-hydroxy-5-methylbenzyl, a group —$CH_2$—$CH(OR^3)$—$R^4$, and a group of the formula —$(CH_2)_m$—$C(O)$—Z where Z is a group selected from —O—$R^5$ and —$N(R^6)(R^7)$ when m is 1 or 0 and when m is 0, Z can be a group —$C(O)$—$OR^8$;

$R^3$ is selected from hydrogen, an aliphatic group of 1–18 carbon atoms described above, an araliphatic group such as benzyl and phenethyl, and an alkanoyl having 2–18 carbon atoms;

$R^4$ is selected from hydrogen, an alkyl group of 1–16 carbon atoms and phenyl;

$R^5$ is selected from an alkyl group of 1–18 carbon atoms, a cycloalkyl group of 5–12 carbon atoms such as cyclopentyl, cyclohexyl, cyclooctyl, cyclododecyl, allyl, benzyl, phenyl, and the group R wherein $R^1$ and $R^2$ are as described above;

$R^6$ and $R^7$, same or different, are selected from hydrogen, an alkyl group having 1–8 carbon atoms such as methyl, ethyl, hexyl, a cycloalkyl group having 5–12 carbon atoms such as those of $R^2$, aryl groups having 6–10 carbon atoms such as 4-methylphenyl, 2-methylphenyl, 4-butylphenyl, and aralkyl groups having 7–15 carbon atoms such as benzyl, o,m,p-alkylsubstituted benzyl, and phenethyl. In addition, $R^6$ and $R^7$, together with the N-atom to which they are attached can form a 5–7 membered ring such as pyrrolidine, piperidine and homopiperidine;

$R^8$ is selected from an alkyl group of 1–18 carbon atoms, phenyl, or benzyl, and is preferably methyl or ethyl.

Y is selected from —O—, —NH— and —$NR^9$; and

B is a divalent alkylene group having 1–10 carbon atoms that may be straight-chained or branched; and —$NR^9$ is an alkyl group of 1–20 carbon atoms or the group R where $R^1$ and $R^2$ are as previously described.

The compounds of formula I can be prepared by the reaction of the functionalized melamine of formula II

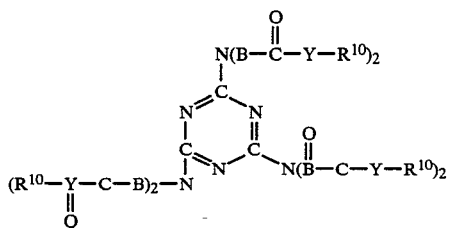

where $R^9$ is lower alkyl such as methyl or ethyl with the appropriately substituted alcohol or amine of formula III;

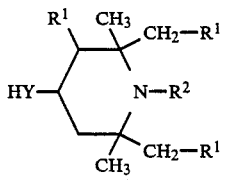

where Y is —O—, —NH— or —NR$^9$—;

The reaction solvent is generally carried out in the presence of a solvent such as ligroine or xylene, or any other solvent suitable for the reaction to occur at or near the reflux temperature of the solvent. The reaction is best carried out using a catalyst such as lithium amide or titanium tetraisopropoxide as well as others suitable for the reaction to occur. The products of this invention may be isolated from the solvent solution and are generally purified by crystallization, trituration or any other suitable method.

The compounds of Formula II can be prepared by the reaction of the appropriate iminodialkylene ester or acid with cyanuric chloride to yield the corresponding melamine hexaalkylene compound. The hexaacid is generally converted into the hexamethyl or hexaethyl ester prior to conversion into the desired compound of the invention.

An alternative means to obtain the compounds of formula I is to react compounds of the formula IV

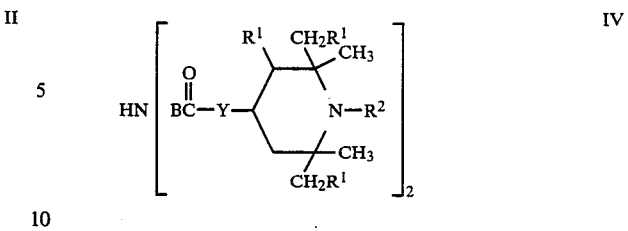

with cyanuric chloride in a solvent such as dioxane, toluene or any other solvent so long as it does not interfere with the reaction, at or near the reflux temperature of the solvent, in the presence of a base such as carbonate, hydroxide, and the like, for the removal of the generated hydrogen chloride.

The starting compound of formula II where B is methylene, Y is —O— and $R^9$ is methyl has been described previously in Ger. Offen. 1,935,010 (1971). The synthetic scheme entails a multi-step sequence as shown below.

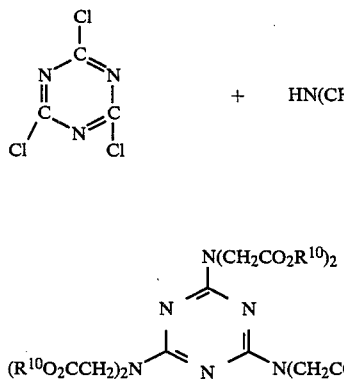
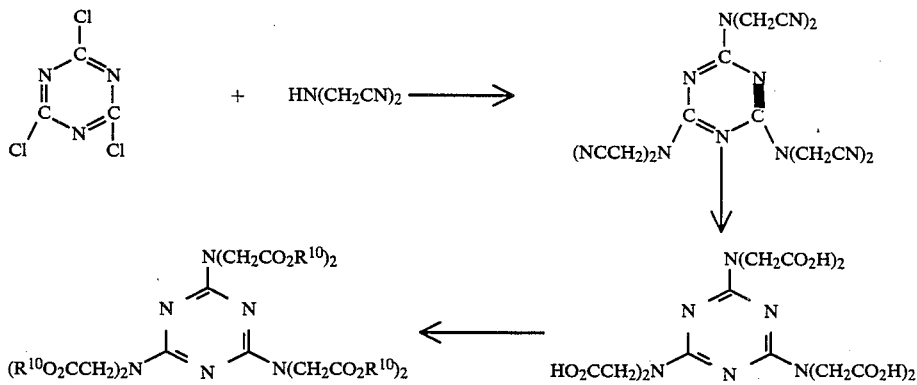

This sequence involves reacting imino diacetonitrile with cyanuric chloride to yield melamine hexaacetonitrile, followed by hydrolysis and subsequent esterification to yield the hexaester.

These esters are then transesterified or amidated with the desired alcohol or amine either in the presence of a solvent or neat, in the presence of a catalyst as known in the art, to give the compounds of the invention. Examples of appropriate solvents without introducing any limitations are ligroine, xylene, toluene, etc., or a mixture thereof. Examples of suitable catalysts are, without introducing any limitations, lithium amide and titanium tetraisopropoxide.

The reaction will generally be carried out at or near the reflux temperature of the solvent when one is used, otherwise the temperature is between 100° and 200° C. The product of the reaction can usually be isolated by partitioning the reaction mixture between water and the solvent of the reaction and subsequent removal of the solvent. The products can be purified by recrystallization or any other suitable method.

The 4-hydroxypolyalkylpiperidine and the 4-aminopolyalkylpiperidines used to convert the esters of formula II into the compounds of the invention are known from German Patent No. 2,352,658 and U.S. Pat. No. 3,684,765. In general, the 4-hydroxy compounds are prepared by reduction via catalytic hydrogenation over Raney Nickel and the 4-amino compounds are synthesized via a reductive amination using ammonia.

The 4-oxopiperidines of formula V can be prepared by the reaction of ammonia with an aliphatic ketone. The reaction of ammonia with acetone to yield triacetoneamine is well-known and various processes exist in the art for its manufacture. The reaction of ammonia with methyl ethyl ketone has been described by W. Traube in Chem. Ber. 41, 777 (1908).

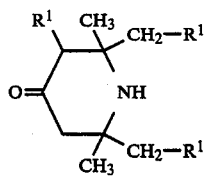

Compounds of the formula V which carry alternative alkyl substituents in the 2-position and the 6-position can be prepared in a two-step process following the procedures outlined in Hel. Chem. Acta 30, 1114 (1947) and Monatsh. Chem. 88, 464 (1957), followed by hydrolysis of the resulting pyrimidine.

The introduction of an alkyl, alkenyl, alkynyl, aralkyl, and 2,3-epoxypropyl group can be achieved by reaction of the initially prepared 4-oxo-piperidine or the derivatized melamine which contains the free N—H of the piperidine with the suitable halide. Examples of suitable halides include methyl iodide, methyl chloride, ethyl bromide, dodecyl chloride, octadecyl chloride, allyl bromide, methallyl chloride, butenyl chloride propargyl chloride, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

An alternative way of preparing the compounds of the invention which contain a N-alkyl, N-alkyenyl, N-alkynyl, N-aralkyl, or 2,3-epoxypropyl group, especially when the desired invention compound is an ester, is to prepare the N-substituted polyalkyl piperidin-4-ol as described in U.S. Pat. No. 4,014,887 and perform the transesterification in the manner as stated previously.

The introduction of an alkyanoyl or an alkenoyl group can be performed by acylation of the N—H group using the suitable acid halide or, when convenient, the acid anhydride. If the acid halide is used, the generated hydrogen halide can be scavenged in the same manner as stated previously. Examples of such groups are acetyl chloride, acetic anhydride, proprionic anhydride, hexanoyl chloride, dodecanoyl chloride, and octadecanoyl chloride.

For the introduction of the group —CH$_2$CH(O—R$^3$)—R$^4$ the substituent can be introduced by reaction of the parent N—H compound with the corresponding alkylene oxide such as ethylene oxide, propylene oxide and styrene oxide. The resulting hydroxy compound can be acylated in the manner commonly known in the art using the suitable acid halide and can be alkylated by formation of the alkoxide and reaction with the desired alkyl halide.

When R is the group —(CH$_2$)$_m$—C(O)—Z and m is zero the appropriate group can be attached by reacting the parent N—H compound with a chloroformate such as methyl chloroformate, ethyl chloroformate, allyl chloroformate, hexyl chloroformate, decyl chloroformate, octadecyl chloroformate, and phenyl chloroformate. The preparation of the oxamide half esters can be achieved by the reaction of the N—H compound with the oxalyl chloride monoalkyl ester such as oxalyl chloride monoethyl ester and scavenging the generated hydrogen chloride as stated previously.

When R is the group —(CH$_2$)$_m$—C(O)—Z and m is 1, the appropriate group can be attached by reacting the parent N—H compound with the appropriate ester of chloroacetic acid such as methyl chloroacetate, ethyl chloroacetate, allyl chloroacetate, phenyl chloroacetate, and cyclohexyl chloroacetate.

The preparation of the corresponding ureas can be achieved by treating the parent N—H compound with the suitable carbamyl halide such as methyl carbamyl chloride, ethyl carbamyl chloride, dimethyl carbamyl chloride, phenyl carbamyl chloride, pyrrolidine carbamyl chloride, and piperidine carbamyl chloride. Alternatively the ureas can be prepared by treating the parent N—H compound with the suitable isocyanate.

For R$^2$ as the oxyl group or hydroxyl group the parent N—H compound can be treated with an oxidizing agent such as hydrogen peroxide in the presence of a catalyst like sodium tungstate or with a percarboxylic acid, like metachloroperbenzoic acid, with subsequent reduction of the oxyl by catalytic hydrogenation if the hydroxyl is desired.

The compounds of this invention are effective light stabilizers for synthetic organic polymers. The following nonlimiting examples are offered to demonstrate the invention:

Melamine hexaacetic acid, hexaester with 2,2,6,6-tetramethyl-4-piperidinol,

Melamine hexaacetic acid, hexaester with 1,2,2,6,6-pentamethyl-4-piperidinol,

Melamine hexaacetic acid, hexaester with 1-butyl-2,2,6,6-tetramethyl-4-piperidinol, Melamine hexaacetic acid, hexaester with 1-allyl-2,2,6,6-tetramethyl-4-piperidinol, Melamine hexaacetic acid, hexaester with 1-oxyl-2,2,6,6-tetramethyl-4-piperidinol, Melamine hexaacetic acid, hexaester with 1-acetyl-2,2,6,6-tetramethyl-4-piperidinol, Melamine hexaacetic acid, hexaamide with 4-amino-2,2,6,6-tetramethylpiperidine Melamine hexapropionic acid, hexaester with 2,2,6,6-tetramethyl-4-piperidinol, Melamine hexahexanoic acid, hexaester with 2,2,6,6-tetramethyl-4-piperidinol, Melamine hexaoctanoic acid, hexaester with 2,2,6,6-tetramethyl-4-piperidinol, Melamine hexadecanoic acid, hexaester with 2,2,6,6-tetramethyl-4-piperidinol, and Melamine hexaundecanoic acid, hexaester with 2,2,6,6-tetramethyl-4-piperidinol.

The compounds of this invention are effective light stabilizers for synthetic organic polymers. In addition to their effective light stabilizing properties, some of the compounds of this invention also exhibit excellent thermal stabilizing performance. Among the synthetic organic polymers which can be stabilized by the compounds of this invention are the polyolefins which include homopolymers of olefins like polyethylene, both high- and low-density polyethylene, polypropylene, polybutadiene, polystyrene, and the like; and copolymers of olefins with other ethylenically unsaturated monomers such as ethylene-propylene copolymer, ethylene-butylene copolymer, ethylene-vinyl acetate copolymer, styrene-butadiene copolymer and the like;

terpolymers such as acrylo-nitrile-butadiene-styrene and the like; polyvinyl chlorides, polyvinylidene chlorides, copolymers of vinyl chloride and vinylidene chloride with vinyl acetate or other ethylenically unsaturated monomer; polyacetals such as polyoxymethylene and polyoxyethylene; polyesters such as polyethylene terephthalate; polyamides such as polyamide 6, polyamide 6,6, polyamide 6,10; polyurethanes and polymers derived from α,β-unsaturated acids and derivatives thereof; polycarbonates; polyacrylates and polymethacrylates, polyacrylic amides and polyacrylonitrile, as well as copolymers of acrylic acid and one or more of its derivatives with a melamine-formaldehyde resin.

Of particular importance among these groups of polymers if the stabilization of polyolefins. The compounds of this invention are excellent for their stabilization. Generally the stabilizers of the invention are added to the polymer to be stabilized in an amount ranging from 0.01 to 5.0% by weight based on the weight of the polymer to be stabilized. Preferably they may be used in an amount between 0.5 and 1% by weight.

The compounds of the invention may also be used in conjunction with other stabilizers for the preparation of stabilized compositions. Among these other additives may be antioxidants, supplemental light stabilizers such as UV absorbers or other hindered amines, metal deactivators, etc., pigments, colorants, fillers, flame retardants, antistatic agents, and the like.

Suitable antioxidants include those of the hindered phenol type such as 2,6-di-t-butyl-p-cresol; 2,4,6-tri-t-butylphenol); 2,2'-thiobis(4-methyl-6-t-butylphenol); octadecyl-3-(3',5'-di-t-butyl-4'-hydroxyphenyl)propionate; pentaerythrityl tetrakis(3',5'-di-t-butyl-4-hydroxyphenyl)propionate; 1,3,5-tris(3',5'-di-t-butyl-4'-hydroxybenzyl) isocyanurate; 1,3,5-tris (2,6-dimethyl-4-t-butyl-3-hydroxybenzyl) isocyanurate; 3,5-di-t-butyl-4-hydroxyhydrocinnamic acid triester with 1,3,5-tris(2-hydroxyethyl)-s-triazine-2,4,6-(1H,3H,5H) trione;

Esters of thiodipropionic acid such as dilaurylthiodipropionate and distearylthiodipropionate are also included.

Phosphites such as triphenyl phosphite, trinonylphenyl phosphite, distearyl pentaerythrityl diphosphite, diphenyldecyl phosphite, tris-(2,4-di-t-butylphenyl)-phosphite, bis(2,4-di-t-butylphenyl)pentaerythritol diphosphite can be used.

Supplemental light stabilizers such as those of the benzotrizole class including 2-(2'hydroxy-5'-t-octylphenyl)benzotriazole; 2-(2'-hydroxy-3',5'-di-t-butylphenyl)-5-chlorobenzotriazole; 2-(2'hydroxy-5'-methylphenyl)benzotriazole; 2-(2'-hydroxy-3'-t-butyl-5'-methylphenyl)benzotriazole; 2-(2'-hydroxy-3',5'-di-t-amylphenyl)benzotriazole; those of the hydroxybenzophenone type such as 2-hydroxy-4-methoxybenzophenone; 2-hydroxy-4-octyloxybenzophenone; 2,2'-dihydroxy-4,4'-dimethoxybenzophenone;

Esters of hindered phenols such as n-hexadecyl-3,5-di-t-butyl-4-hydroxybenzoate and 2',4'-di-t-butylphenyl-3,5-di-t-butyl-4-hydroxybenzoate;

Metal complexes such as nickel complexes of 2,2'-thiobis-(4-tert-octylphenol), nickel dibutyl dithiocarbamate; nickel salts of 3,5-di-t-butyl-4-hydroxybenzylphosphonic acid monoalkyl esters where alkyl is methyl, ethyl, propyl and butyl, and nickel complexes of 2-hydroxy-4-methylphenylundecylketoneoxime.

Other examples of suitable supplemental light stabilizers may be found in U.S. Pat. Nos. 3,488,290 and 3,496,134.

The following nonlimiting preparative examples are given to illustrate the invention wherein all expressed proportions are by weight unless otherwise specified.

EXAMPLE 1

Preparation of melamine hexaacetic acid, hexaester with 2,2,6,6-tetramethyl-4-piperidinol A mixture of melamine hexaacetic acid, hexamethylester (4.26 g), prepared according to the procedure of Ger. Offen. 1,935,010, and 2,2,6,6-tetramethyl-4-piperidinol (7.92 g) was diluted with 50 ml of ligroine and heated to reflux. Lithium amide (33 mg) was added as well as 50 ml additional ligroine. The distillate was gradually removed for 2 hours and the mixture was permitted to reflux 16 hrs. Workup was effected by adding additional solvent, washing with water, drying (MgSO$_4$), and concentrating. The solid residue was recrystallized from ligroine to yield 5.4 g of the product (mp 115°–118° C.).

EXAMPLE 2

Preparation of melamine hexaacetic acid, hexaester with 1,2,2,6,6-pentamethyl-4-piperidinol A mixture of melamine hexaacetic acid, hexamethyl ester (4.0 g) and 1,2,2,6,6-pentamethyl-4-piperidinol (8.1 g) was combined in xylene (15 ml) and heated to 100°–105° C. At this point the catalyst, titanium tetraisopropyl titanate (0.15 ml), was added. The homogeneous mixture was heated to about 140° C. and maintained for 16 hours with gradual removal of the produced methanol. After this time the mixture was cooled, dissolved in CH$_2$Cl$_2$ and washed with water. After backwashing the aqueous portion with CH$_2$Cl$_2$, the organic extracts were dried (MgSO$_4$) and concentrated to yield a white solid. Recrystallization from ligroine yielded 7.8 g of the product (mp 65°–75° C.).

EXAMPLES 3–5

In order to further illustrate the effectiveness of the above-described compounds as light stabilizers, the materials described by Examples 1 and 2 were each incorporated into a commercially available polypropylene resin manufactured by Hercules Corporation as Pro-Fax 6301 Polypropylene Resin. The light stabilizers were incorporated into the polypropylene by solvent blending methylene chloride at a concentration of 0.25% by weight of the total resin composition. A primary antioxidant (stearyl beta(3,5-di-t-butyl-4-hydroxyphenylpropionate)) was used at a level of 0.2%. The resin was then extruded at 200° C. and compression molded at 6,000 psi at 188° C. to produce films having a thickness of 5 mils. A control film was also produced by an identical procedure with the light stabilizer omitted. Each film was exposed to a Xenon Art in an Atlas Weather-o-Meter until the IR carbonyl increase by 0.5, which is considered to be the failure point.

TABLE 1

| Example # | Stabilizer | Hrs. to Failure |
| --- | --- | --- |
| 3 | Control | 900 |
| 4 | Compound 1 | >4000 |
| 5 | Compound 2 | >4000 |

What is claimed is:
1. A compound of the formula

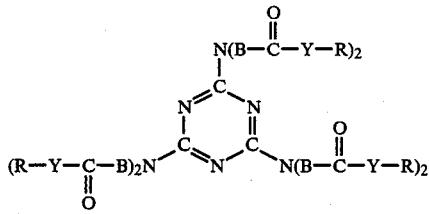

wherein R is the group

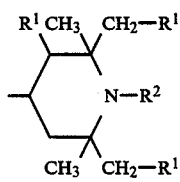

$R^1$ is selected from hydrogen and an alkyl group of 1-5 carbon atoms, $R^2$ is selected from the group consisting of hydrogen, oxyl, hydroxyl, a straight or branched chain methylene-linked alkyl group of 1-18 carbon atoms, an alkanoyl group having 2-18 carbon atoms, an alkenyl group of 3-4 carbon atoms, an alkenoyl group of 3-6 carbon atoms, an alkynyl group of 3-6 carbon atoms, a cyanomethyl group, a 2,3-epoxypropyl group, a benzyl or alkylbenzyl group of 7-15 carbon atoms, a group —CH$_2$CH(OR$^3$)—R$^4$ and a group of the formula —(CH$_2$)$_m$—C(O)—Z wherein Z is a group selected from OR$^5$ and —N(R$^6$)(R$^7$) when m is 1 or 0 and when m is 0, Z can be a group —C(O)—OR$^8$, $R^3$ is selected from the group consisting of hydrogen, an aliphatic group of 1-18 carbon atoms, an araliphatic group and an alkanoyl group, $R^4$ is selected from the group consisting of hydrogen, an alkyl group of 1-16 carbon atoms and phenyl, $R^5$ is selected from the group consisting of an alkyl group of 1-18 carbon atoms, a cycloalkyl group of 5-12 carbon atoms, allyl, benzyl, phenyl, and a group of R, $R^6$ and $R^7$, same or different, are selected from the group consisting of hydrogen, an alkyl group having 1-8 carbon atoms, a cycloalkyl group having 5-12 carbon atoms, an alkaryl group having 6-10 carbon atoms, an aralkyl group having 7-15 carbon atoms, and additionally $R^6$ and $R^7$, together with the N-atom to which they are attached, can form a 5-7 membered ring consisting of pyrrolidine, piperidine, and homopiperidine, and $R^8$ is selected from the group consisting of an alkyl group of 1-18 carbon atoms, phenyl and benzyl, B is a divalent alkylene group having 1-10 carbon atoms, Y is selected from —O— and —NH—; and —NR$^9$ where $R^9$ is an alkyl group of 1-20 carbon atoms or the group R where $R^1$ and $R^2$ are as previously described.

2. A compound of claim 1 wherein $R^1$ is H and Y is —O—.

3. A compound of claim 2 wherein B is methylene.

4. A compound of claim 3 wherein $R^2$ is hydrogen.

5. A compound of claim 3 wherein $R^2$ is methyl.

6. A synthetic polymer composition stabilized against light-induced degradation comprising an organic polymer normally subjected to deterioration by light containing from 0.01-5% by weight of a compound of claim 1.

7. A composition of claim 6 wherein the organic polymer is a polyolefin homopolymer or copolymer.

8. A composition of claim 7 wherein said organic polymer is a homo- or copolymer of propylene.

* * * * *